US00PP32532P2

(12) United States Plant Patent
Peasley

(10) Patent No.: US PP32,532 P2
(45) Date of Patent: Dec. 1, 2020

(54) ***MUSA* PLANT NAMED 'FLF-1'**

(50) Latin Name: *Musa hybrida*
Varietal Denomination: FLF-1

(71) Applicant: David Peasley, Farrants Hill (AU)

(72) Inventor: David Peasley, Farrants Hill (AU)

( * ) Notice: Subject to any disclaimer, the term of this patent is extended or adjusted under 35 U.S.C. 154(b) by 0 days.

(21) Appl. No.: 16/602,228

(22) Filed: Aug. 30, 2019

(51) Int. Cl.
*A01H 5/08* (2018.01)
*A01H 6/00* (2018.01)

(52) U.S. Cl.
USPC ..... Plt./160
CPC ..... *A01H 6/00* (2018.05)

(58) Field of Classification Search
USPC ..... Plt./160
CPC ..... A01H 5/08
See application file for complete search history.

(56) References Cited

PUBLICATIONS https://www.farmonline.com.au/story/3369321/race-for-new-banana/; Mar. 14, 2015; 4 pages.*

* cited by examiner

*Primary Examiner* — Kent L Bell
(74) *Attorney, Agent, or Firm* — C. A. Whealy

(57) ABSTRACT

A new and distinct cultivar of *Musa* plant named 'FLF-1', characterized by its upright, sturdy and robust plant habit; vigorous growth habit; medium to large fruit bunches with numerous hands; attractive fruits with good eating quality; complete resistance to Panama Disease Tropical Race 1 (*Fusarium oxysporum cubense* Race 1); strong resistance to Panama Disease Tropical Race 4 (*Fusarium oxysporum cubense* Race 4); strong tolerance to Yellow Sigatoka Leaf Spot (*Pseudocercospora musicola*); and relatively strong cold temperature tolerance in sub-tropical environments.

16 Drawing Sheets

Figure 1:
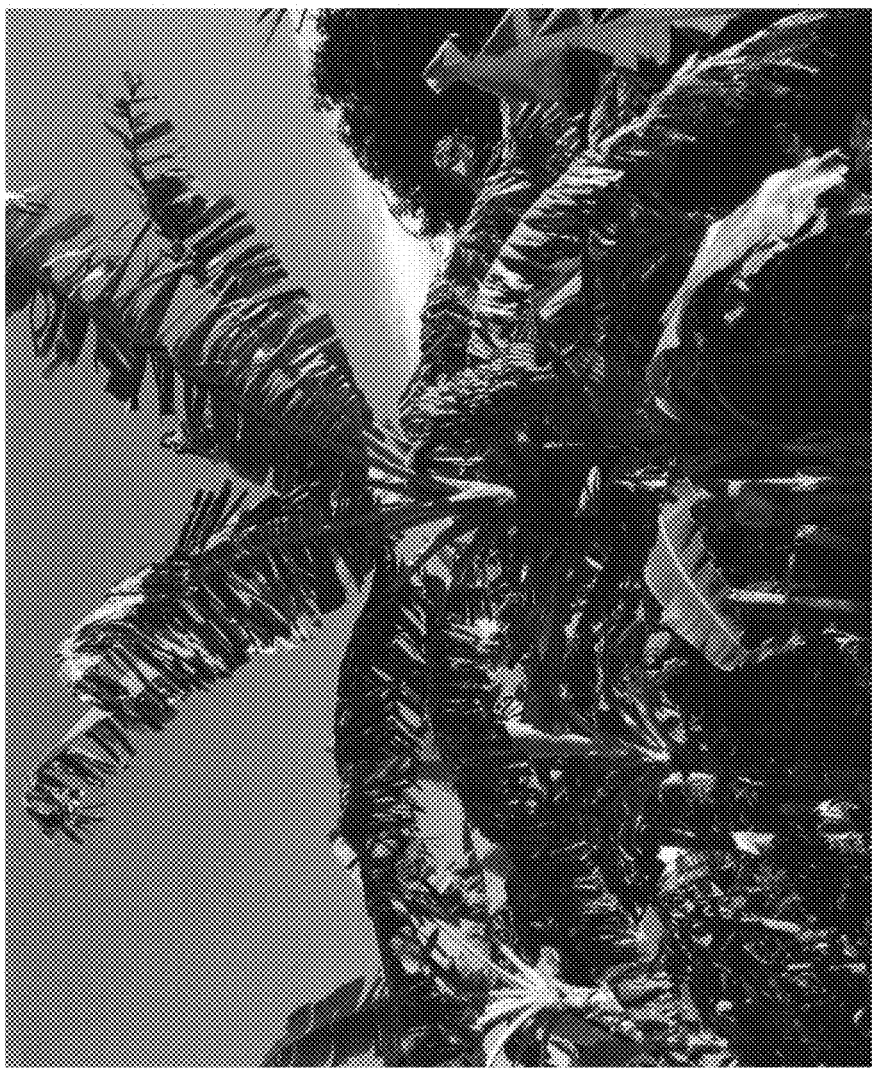
Figure 2:
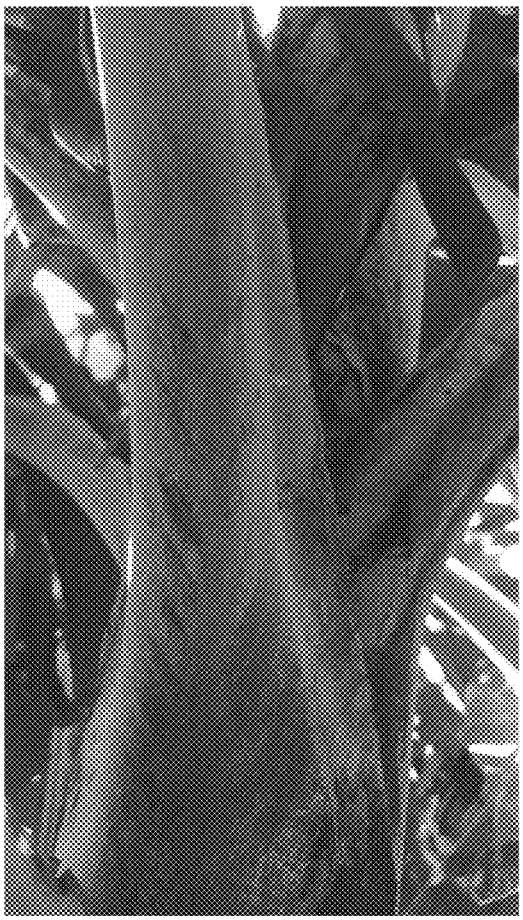
Figure 3:
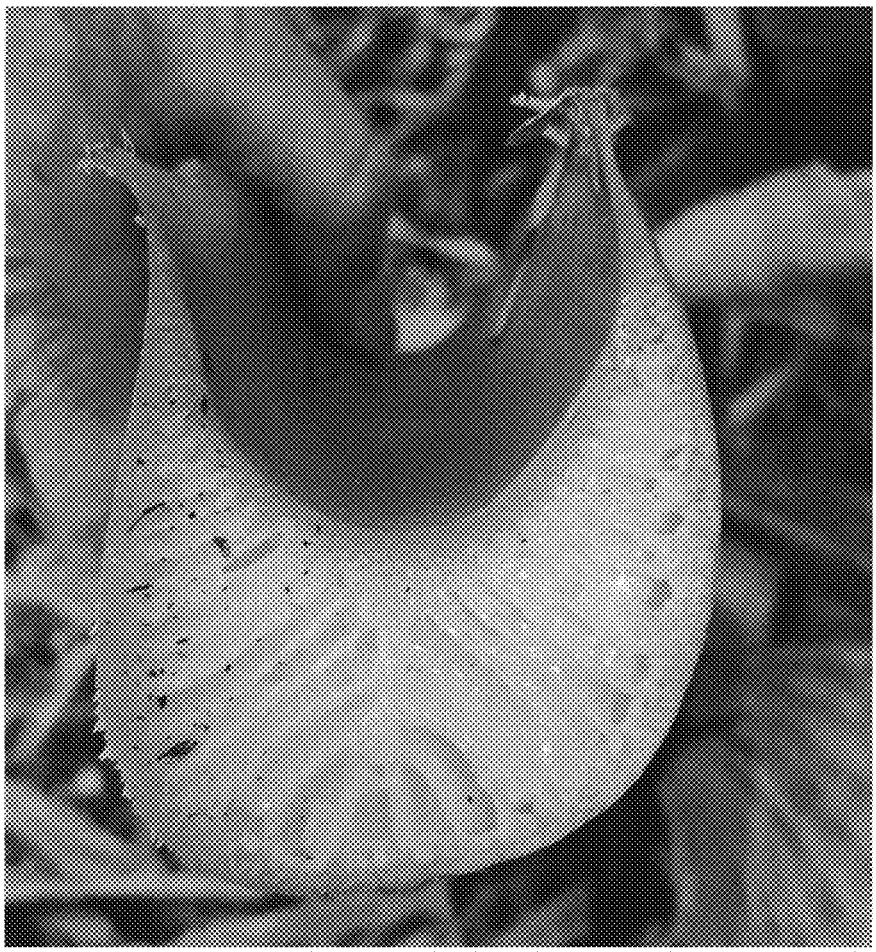
Figure 4:
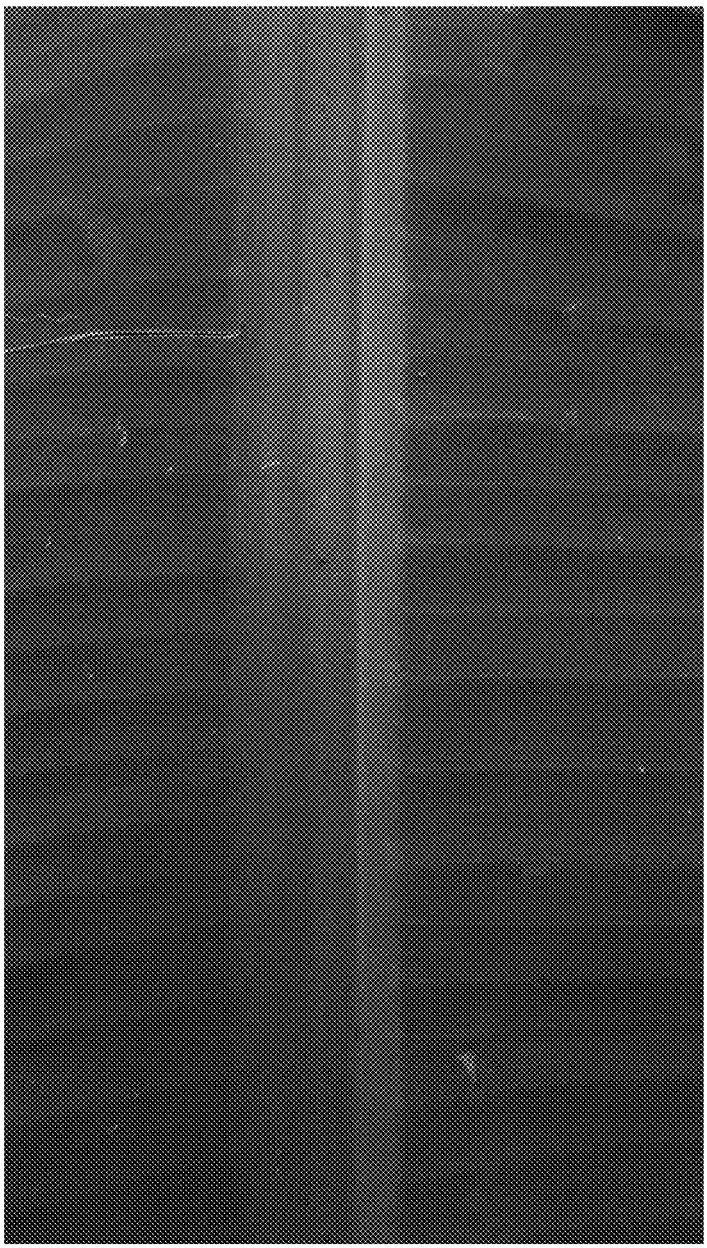
Figure 5:
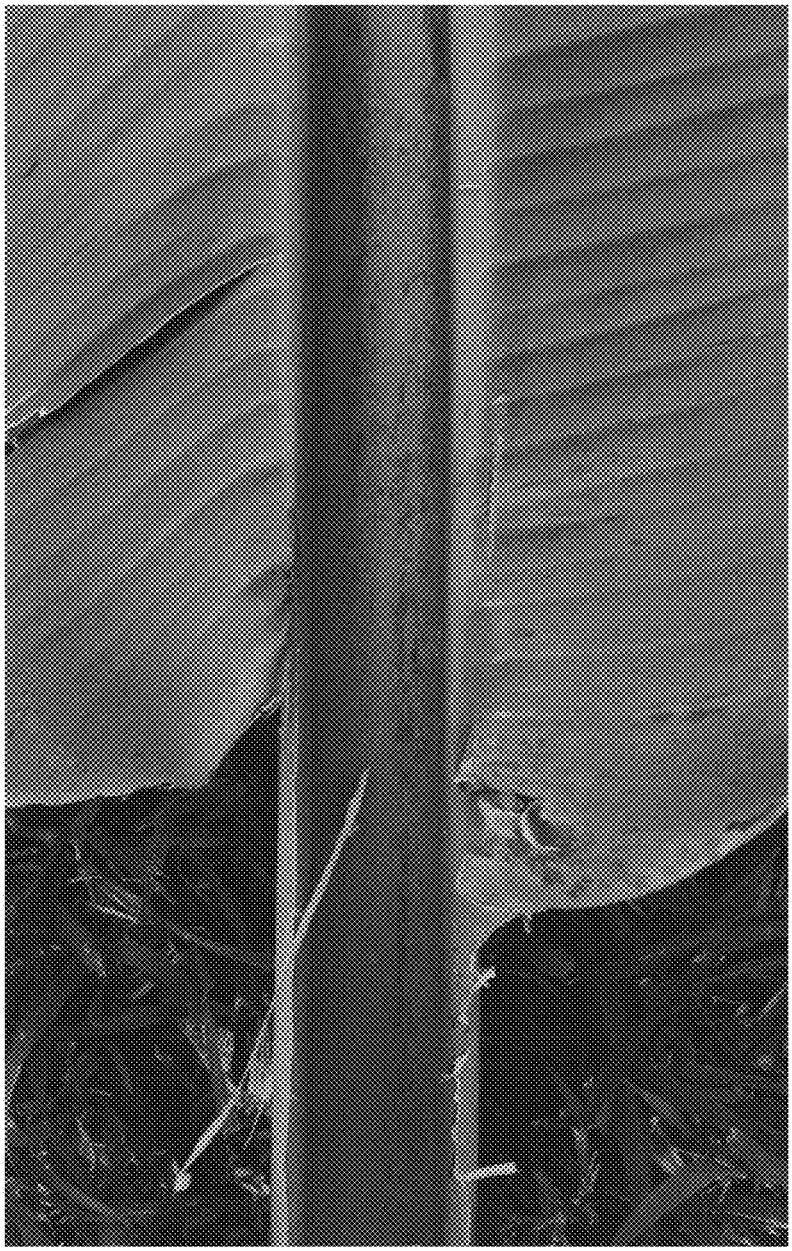
Figure 6:
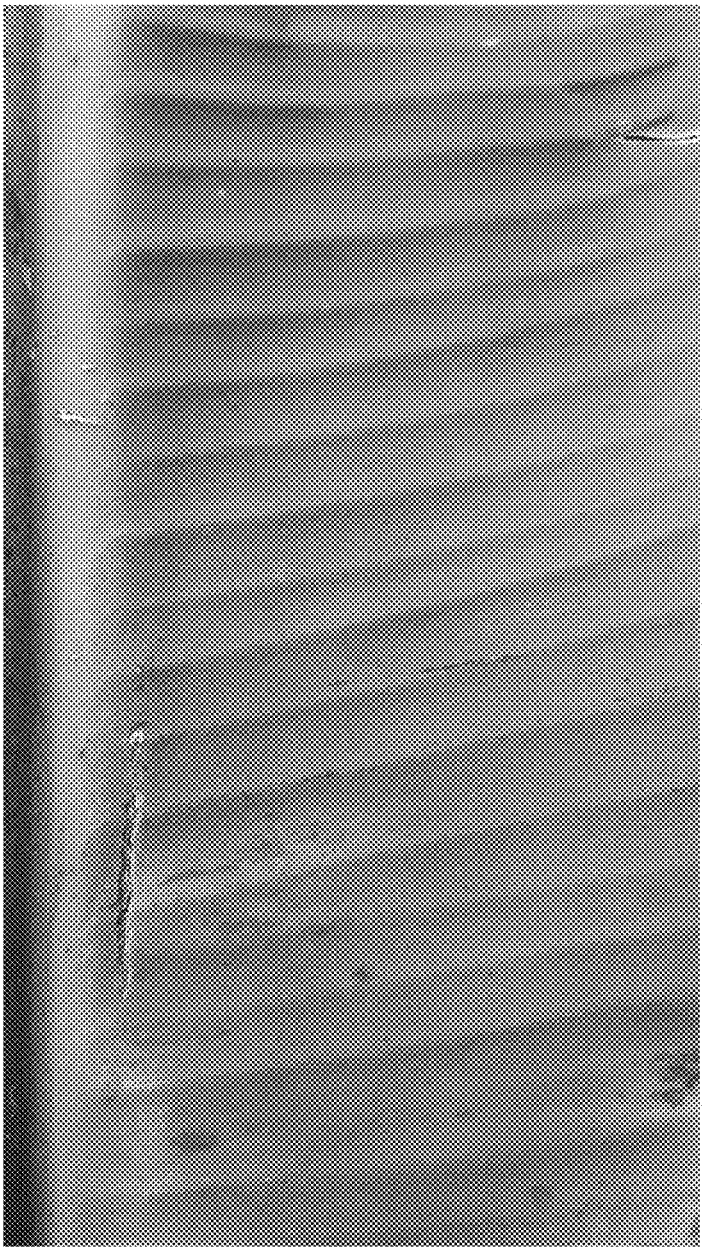
Figure 7:
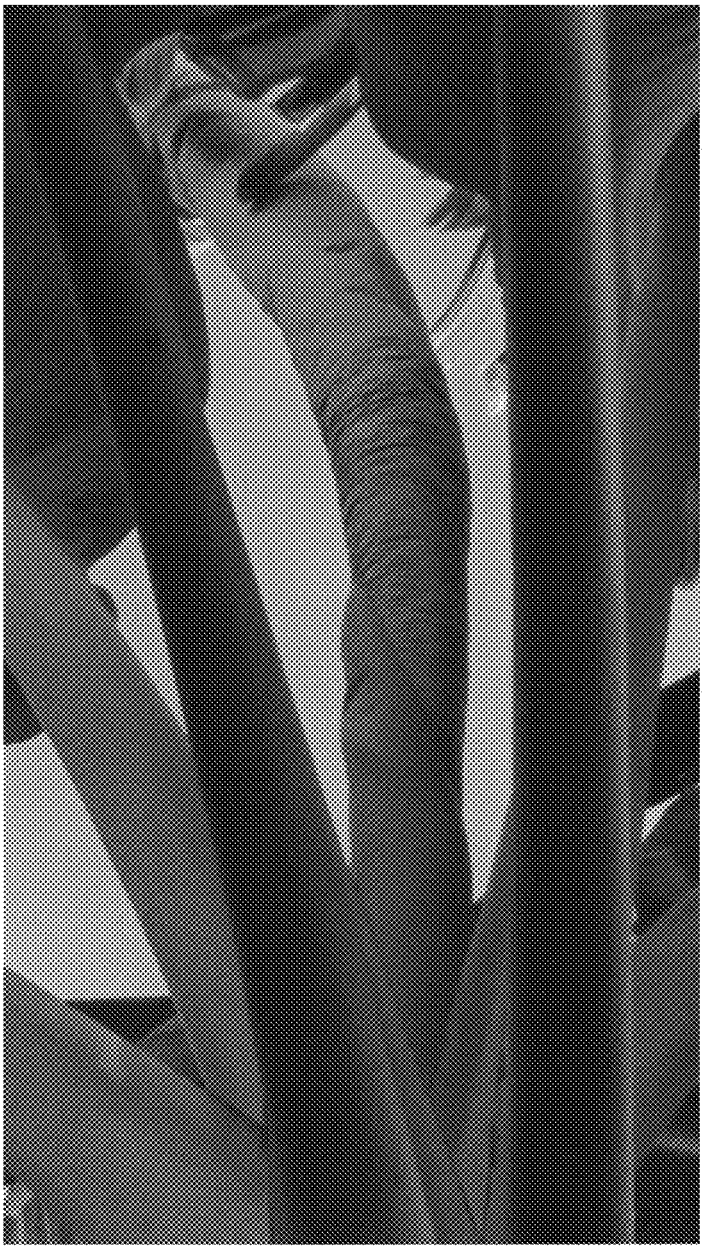
Figure 8:
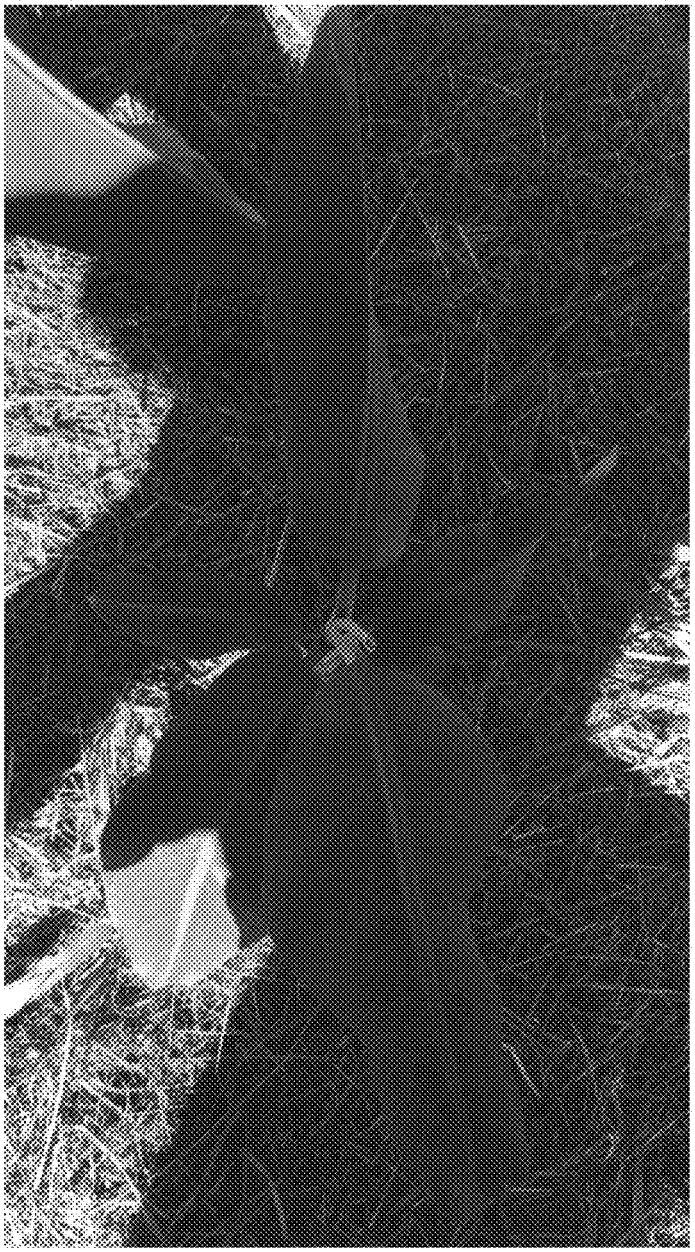
Figure 9:
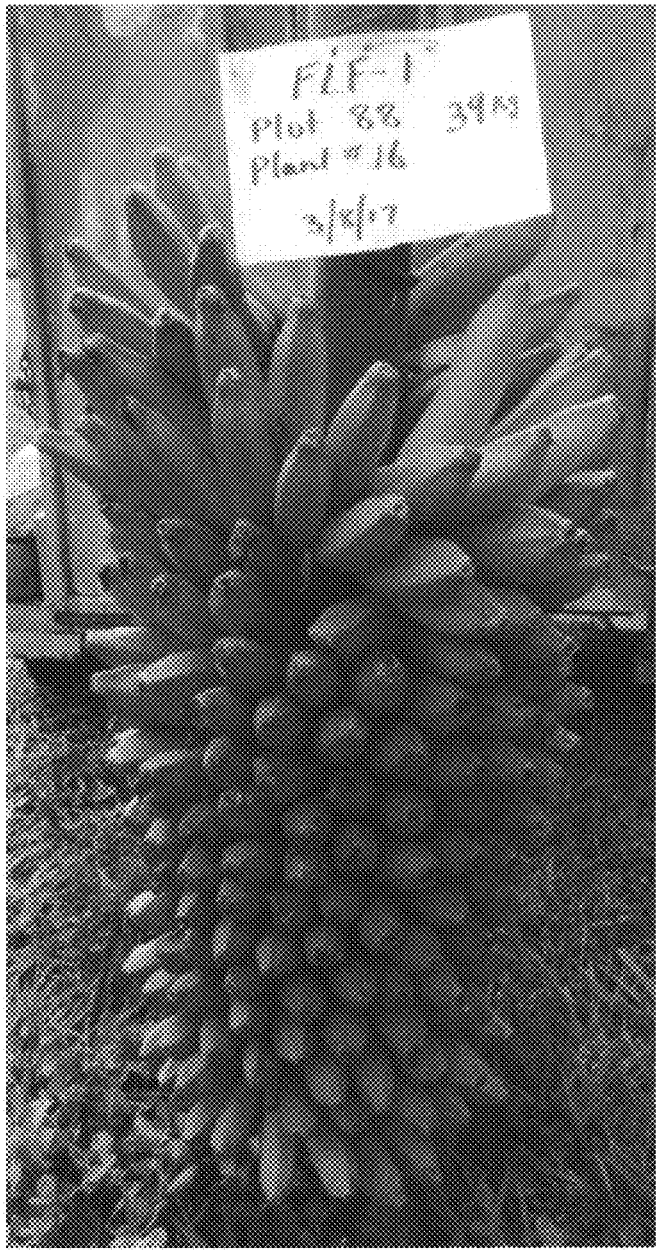
Figure 10:
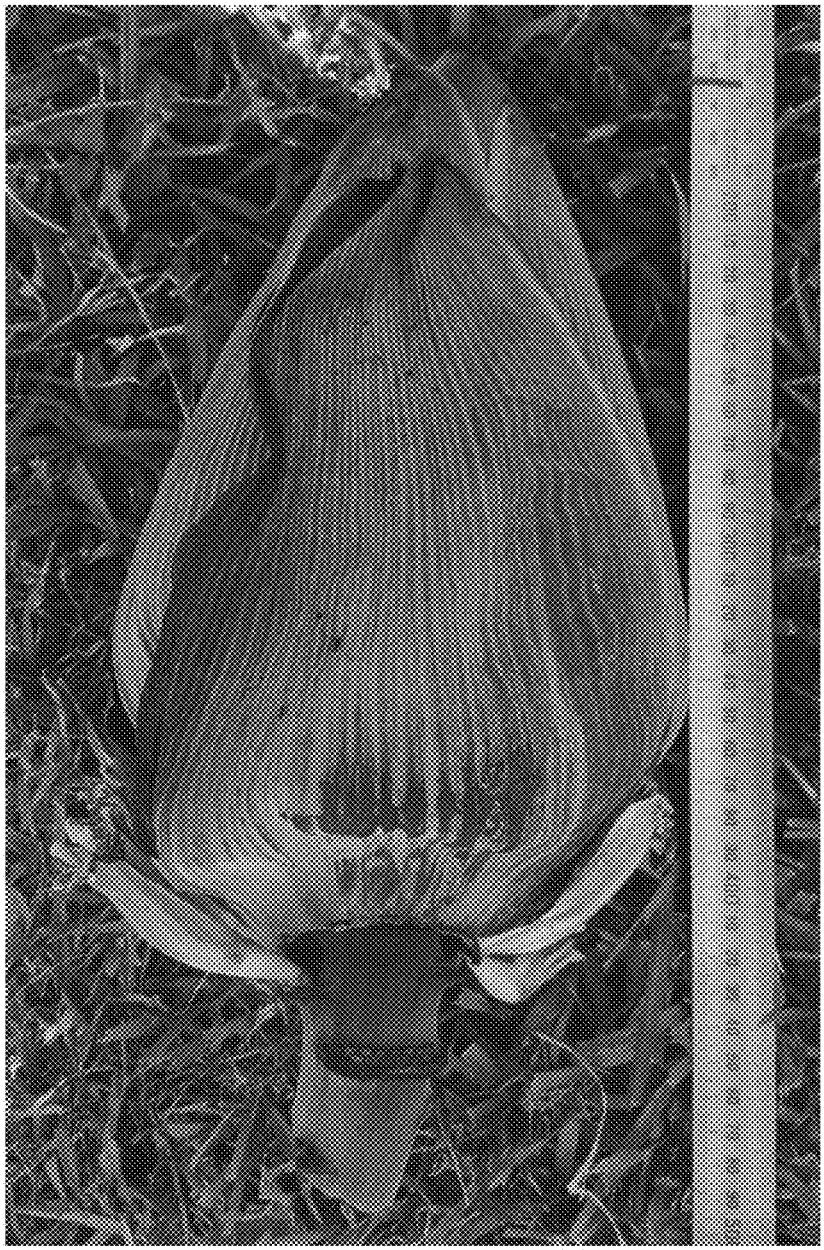
Figure 11:
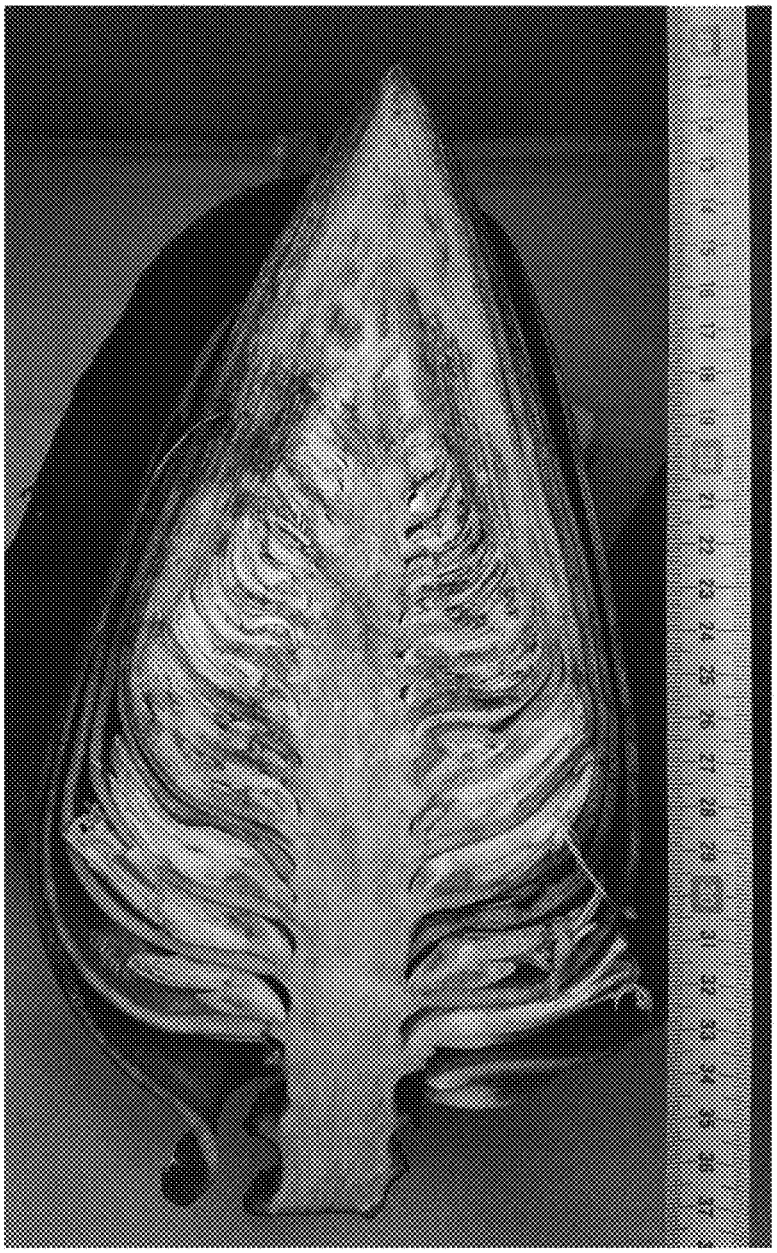
Figure 12:
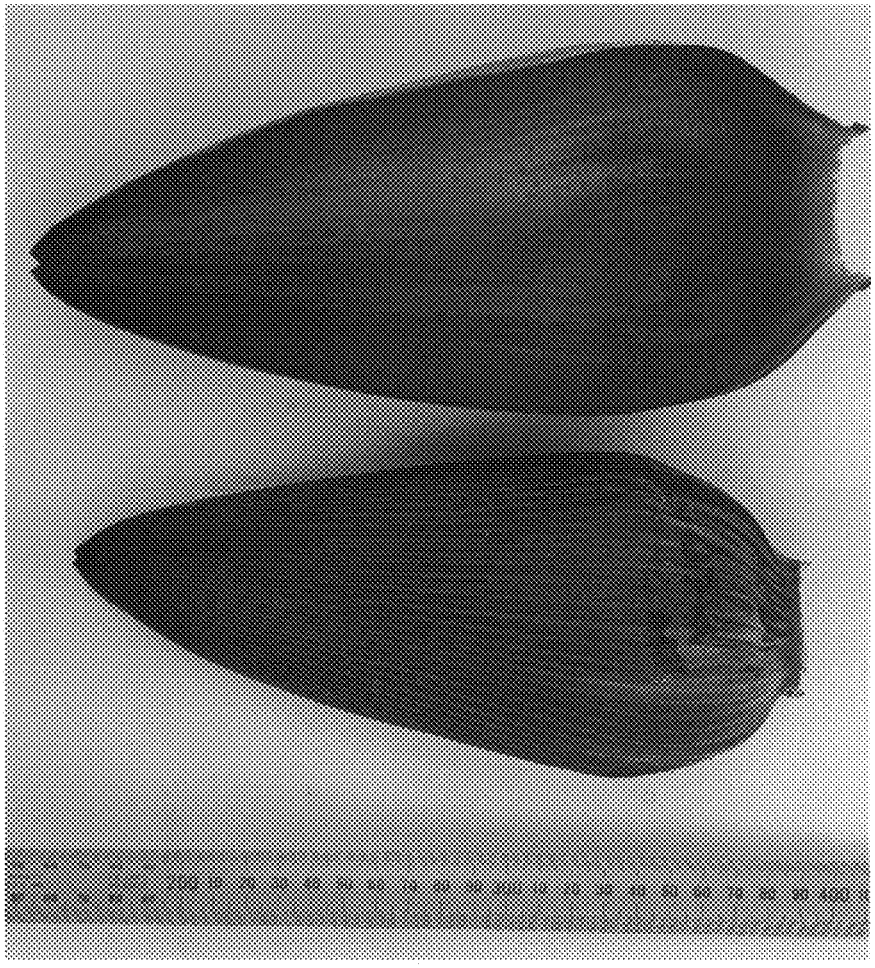
Figure 13:
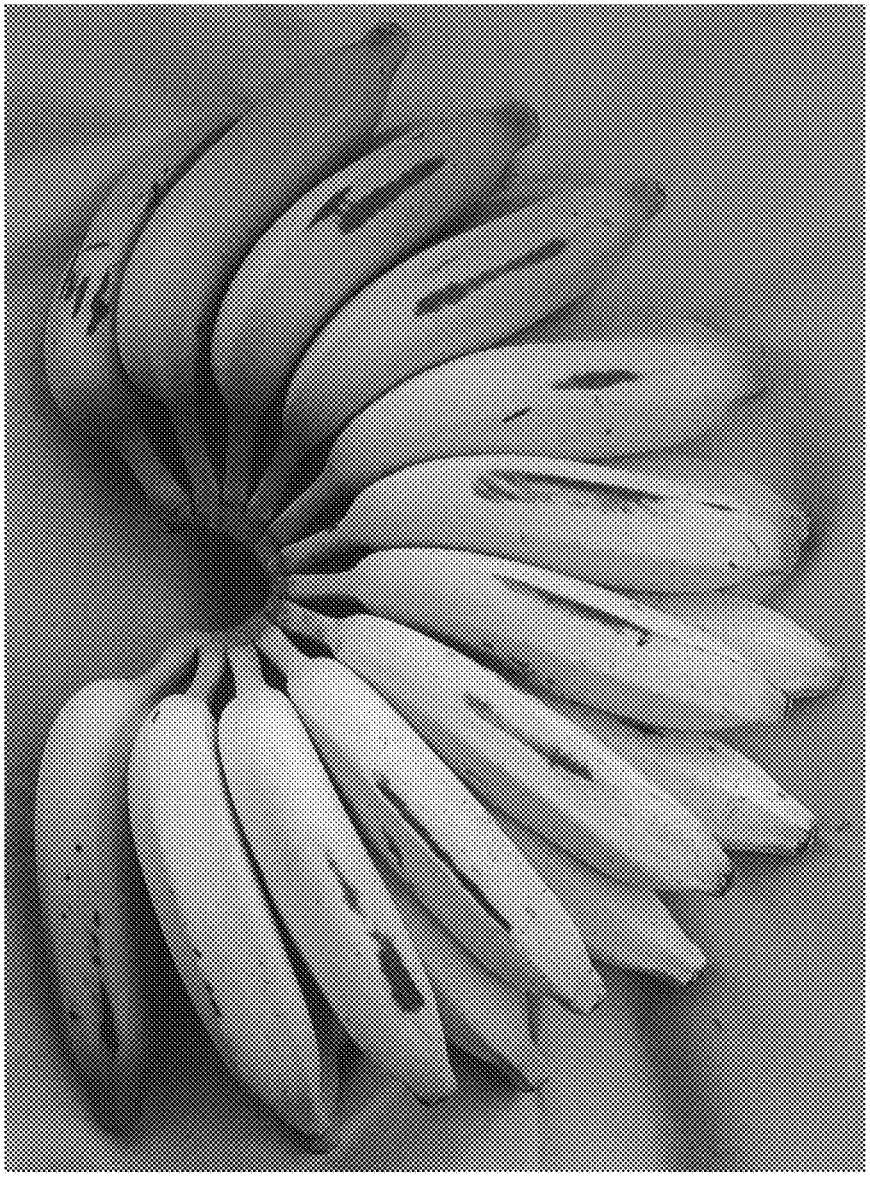
Figure 14:
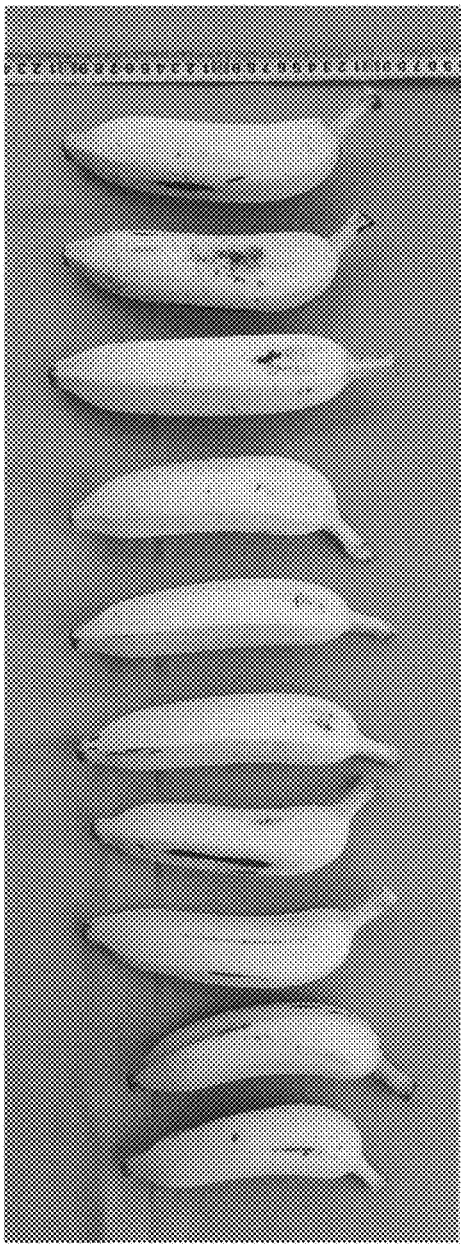
Figure 15:
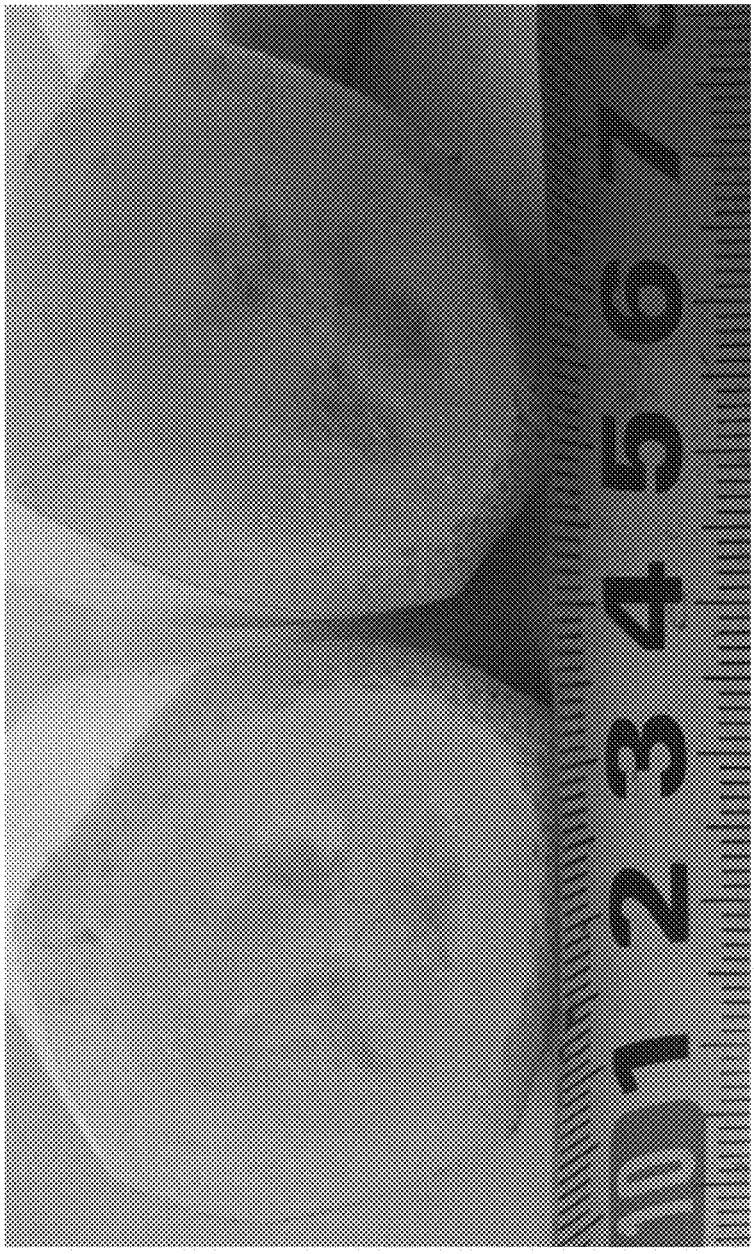
Figure 16:
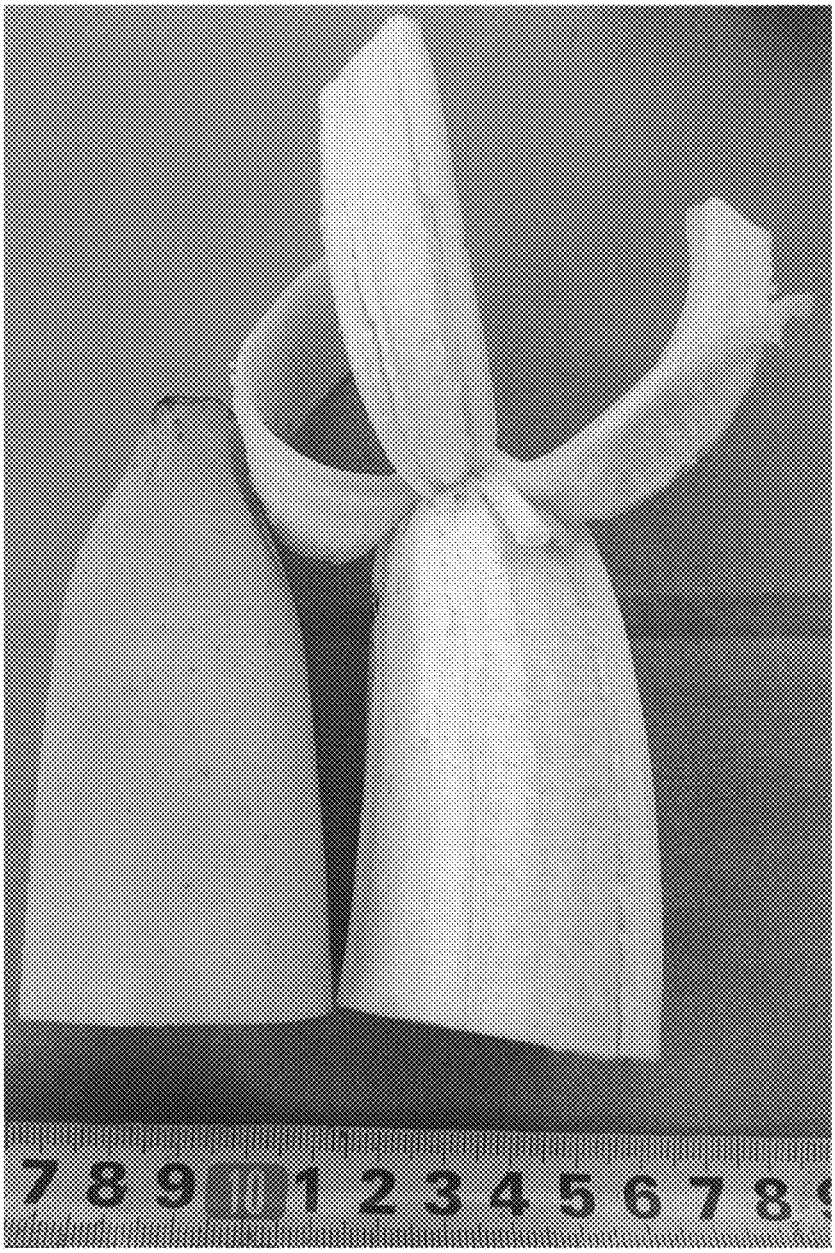

Botanical designation: *Musa hybrida.*
Cultivar denomination: 'FLF-1'.

BACKGROUND OF THE INVENTION

The present invention relates to a new and distinct cultivar of *Musa* plant, botanically known as *Musa hybrida* and hereinafter referred to by the name 'FLF-1'. The new *Musa* plant's market class is a fruiting plant fitting in the dessert banana segment currently filled by the Cavendish and Lady Finger types. The new *Musa* plant is intended for use as fresh fruit for shipping, fresh markets and processing markets.

The new *Musa* plant is a naturally-occurring whole plant mutation of an unnamed Australian Lady Finger type selection, not patented. The new *Musa* plant was discovered and selected by the Inventor as a single plant from within a population of plants of the parent selection in a controlled field plantation environment in Currumbin Valley, Queensland, Australia in November, 2010. The new *Musa* plant was selected on the basis of its strong resistance to Panama Disease Race 1, strong plant growth vigor, large fruit bunch size and good eating quality. The new *Musa* plant was subsequently evaluated over a number of years including field testing at Duranbah, New South Wales, Australia and Farrants Hill, New South Wales, Australia; in vitro meristem propagation and evaluation at Tumbi Umbi, New South Wales, Australia; commercial field plantation evaluation at Whian Whian, New South Wales, Australia; and greenhouse disease tolerance testing at Wageningen, The Netherlands. Disease tolerance testing has confirmed complete resistance to Panama Disease Tropical Race 1 (*Fusarium oxysporum cubense* Race 1), strong resistance to Panama Disease Tropical Race 4 (*Fusarium oxysporum cubense* Race 4) and strong tolerance of Leaf Spot Disease Yellow Sigatoka (*Pseudocercospora musicola*). Field plantation production testing of the new *Musa* plant has demonstrated sturdy robust plants with reduced need for propping, strong cold tolerance in sub-tropical growing conditions compared to the Cavendish type cultivars, reduced production costs compared to the Cavendish type cultivars and potential for closer planting and higher productivity per hectare compared to the Cavendish type cultivars. The new *Musa* plant is suited to cultivation with minimal pesticide use, natural production systems and organic production. Harvest and post-harvest evaluation of the new *Musa* plant has shown higher yield than Lady Finger type cultivars and comparable yield to Cavendish type cultivars. Fruits of the new *Musa* plant are similar in taste to Lady Finger type cultivars. Fruits of the new *Musa* have firm texture, clean skin and attractive yellow coloration.

Asexual reproduction of the new *Musa* plant by in vitro meristem culture since 2012 in Tumbi Umbi, New South Wales, Australia, has shown that the unique features of this new *Musa* plant are stable and reproduced true to type in successive generations.

SUMMARY OF THE INVENTION

Plants of the new *Musa* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'FLF-1'. These characteristics in combination distinguish 'FLF-1' as a new and distinct *Musa* plant:

1. Upright, sturdy and robust plant habit which may not require propping.
2. Vigorous growth habit.
3. Medium to large fruit bunches with numerous hands.
4. Attractive fruits with good eating quality.
5. Complete resistance to Panama Disease Tropical Race 1 (*Fusarium oxysporum cubense* Race 1).
6. Strong resistance to Panama Disease Tropical Race 4 (*Fusarium oxysporum cubense* Race 4).
7. Strong tolerance to Yellow Sigatoka Leaf Spot (*Pseudocercospora musicola*).
8. Relatively strong cold temperature tolerance in sub-tropical environments.

Plants of the new *Musa* differ primarily from plants of the parent selection in the following characteristics:

1. The leaf habit of plants of the new *Musa* plant is drooping whereas the leaf habit of plants of the parent selection is upright.
2. Plants of the new *Musa* are more vigorous than plants of the parent selection.
3. Peduncles of plants of the new *Musa* are longer than peduncles of plants of the parent selection.
4. Plants of the new *Musa* produce larger fruit bunches than plants of the parent selection.
5. Fruit bunches of plants of the new *Musa* are cylindrical in shape whereas fruit bunches of plants of the parent selection are conical in shape.
6. Plants of the new *Musa* produce more hands per bunch than plants of the parent selection.
7. Fruits of plants of the new *Musa* are longer than fruits of plants of the parent selection.
8. Plants of the new *Musa* have complete resistance to Panama Disease Tropical Race 1 whereas plants of the parent selection are susceptible to Panama Disease Tropical Race 1.
9. Plants of the new *Musa* have strong resistance to Panama Disease Tropical Race 4 whereas plants of the parent selection are susceptible to Panama Disease Tropical Race 4.

Plants of the new *Musa* can be compared to plants of *Musa hybrida* 'FHIA-18', not patented. In side-by-side comparisons, plants of the new *Musa* differ primarily from plants of 'FHIA-18' in the following characteristics:

1. The pseudostem tapering on plants of the new *Musa* is not as strong as the pseudostem tapering on plants of the 'FHIA-18'.
2. Peduncles of plants of the new *Musa* are smaller than peduncles of plants of 'FHIA-18'.
3. Fruit bunches of plants of the new *Musa* are shorter in length than fruit bunches of plants of 'FHIA-18'.
4. Fruits of plants of the new *Musa* are shorter in length than fruits of plants of 'FHIA-18'.
5. Male inflorescences of plants of the new *Musa* are narrower than male inflorescences of 'FHIA-18'.
6. Plants of the new *Musa* are more cold tolerant in sub-tropical environments than plants of 'FHIA-18'.

BRIEF DESCRIPTION OF THE PHOTOGRAPHS

The accompanying colored photographs illustrate the overall appearance of the new *Musa* plant showing the colors as true as it is reasonably possible to obtain in colored reproductions of this type. Colors in the photographs may differ slightly from the color values cited in the detailed botanical description which accurately describe the colors of the new *Musa* plant. The photographs are described as follows:

The photograph on the first sheet is a side perspective view of typical plants of 'FLF-1' showing the plant habit;

The photograph on the second sheet is a close-up view of the base of a typical leaf petiole of 'FLF-1';

The photograph on the third sheet is a close-up view of the petiole canal form of 'FLF-1';

The photograph on the fourth sheet is a close-up view of the upper surface of a typical leaf of 'FLF-1';

The photograph on the fifth sheet is a close-up view of the asymmetrical leaf blade insertion of 'FLF-1';

The photograph on the sixth sheet is a close-up view of the lower surface of a typical leaf of 'FLF-1';

The photograph on the seventh sheet is a close-up view of a typical cigar leaf of 'FLF-1';

The photograph on the eighth sheet is a close-up view of typical water sucker leaf blotches of 'FLF-1';

The photograph on the ninth sheet is a close-up view of a typical fruit bunch of 'FLF-1';

The photograph on the tenth sheet is a close-up view of a typical male inflorescence bud of 'FLF-1';

The photograph on the eleventh sheet is a close-up view of a typical male inflorescence bud of 'FLF-1' in longitudinal section;

The photograph on the twelfth sheet is a close-up view showing the typical bract colors of 'FLF-1';

The photograph on the thirteenth sheet is a close-up view of a typical fruit hand of 'FLF-1';

The photograph on the fourteenth sheet is a close-up view of a typical fruits of 'FLF-1';

The photograph on the fifteenth sheet is a close-up view of typical fruits of 'FLF-1' in transverse section; and The photograph on the sixteenth sheet is a close-up view of typical fruits of 'FLF-1' showing the apex, pulp and peel.

DETAILED BOTANICAL DESCRIPTION

The aforementioned photographs and following observations and measurements describe plants of the new *Musa* grown from September, 2017 to May, 2019 in an outdoor nursery in Duranbah, New South Wales, Australia. During the production of the plants, day temperatures ranged from 21° C. to 28° C., night temperatures ranged from 14° C. to 18° C. and light levels ranged from 6 klux to 8 klux. Plants were desuckered and were four years old when the photographs and the description were taken. In the following description, color references are made to The Royal Horticultural Society Colour Chart, 2015 Edition, except where general terms of ordinary dictionary significance are used. The following description is in accordance with the internationally standardized "Descriptors for Banana (*Musa* spp.)" elaborated by IPGRI-INIBAP/CIRAD, 1996 edition.

Botanical classification: *Musa hybrida* 'FLF-1'.

Parentage: Naturally-occurring whole plant mutation of an unnamed Australian Lady Finger type selection, not patented.

Propagation:

*Type*.—By in vitro meristem culture.

*Time to initiate roots*.—About seven to ten days at temperatures ranging about 22° C. to 25° C.

*Time to produce a rooted young plant, summer.*—About four weeks at temperatures ranging from 24° to 30° C.

*Time to produce a rooted young plant, winter.*—About six weeks at temperatures ranging from 16° to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Moderate branching; medium density.

Plant general appearance:

6.1.1 *Leaf habit.*—Drooping.

6.1.2 *Dwarfism.*—Normal type; leaves not overlapped and leaf ratio inferior to 2.5.

Pseudostem/suckers:

6.2.1 *Pseudostem height.*—About 3.5 meters.

6.2.2 *Pseudostem aspect.*—Robust, about 101 cm to 109.0 cm.

6.2.3 *Pseudostem color.*—Close to N144A.

6.2.4 *Pseudostem appearance.*—Shiny, not waxy.

6.2.5 *Predominant underlying color of the pseudostem.*—Close to between N144B and 145A.

6.2.6 *Pigmentation of the underlying pseudostem.*—Close to N187A.

6.2.7 *Sap color.*—Watery.

6.2.8 *Wax on leaf sheaths.*—Moderately waxy.

6.2.9 *Number of suckers.*—Plants are desuckered.

6.2.10 *Development of suckers.*—More than ¾ of the height of the parent plant.

6.2.11 *Position of suckers.*—Close to parent, vertical growth.

Petiole/midrib/leaf:

6.3.1 *Blotches at the petiole base.*—Sparse blotching.

6.3.2 *Blotches color.*—Close to N187A.

6.3.3 *Petiole canal leaf III.*—Wide with erect margins.

6.3.4 *Petiole margins.*—Winged and not clasping the pseudostem.

6.3.5 *Wing type.*—Dry.

6.3.6 *Petiole margin color.*—Close to 138A.

6.3.7 *Edge of the petiole margin.*—Colorless, without a color line.

6.3.8 *Petiole margin width.*—Less than 1 cm.

6.3.9 *Leaf blade length.*—Greater than 261 cm, about 300 cm.

6.3.10 *Leaf blade width.*—Greater than 91 cm, about 94 cm.

6.3.10.1 *Leaf ratio.*—Greater than or equal to 3, about 3.2.

6.3.11 *Petiole length.*—About 60.0 cm.

6.3.12 *Color of leaf upper surface.*—Close to between 138A and 137D.

6.3.13 *Appearance of leaf upper surface.*—Dull.

6.3.14 *Color of the leaf lower surface.*—Close to 138B.

6.3.15 *Appearance of the leaf lower surface.*—Dull.

6.3.16 *Wax on leaves.*—Moderately waxy.

6.3.17 *Insertion point of leave blades on petiole.*—Asymmetric.

6.3.18 *Shape of leaf blade base.*—Both sides rounded.

6.3.19 *Leaf corrugation.*—Very corrugated, even.

6.3.20 *Color of midrib dorsal surface.*—Proximally, close to 152D; distally, close to 138B.

6.3.21 *Color of midrib ventral surface.*—Close to between N144A and 151A.

6.3.22 *Color of cigar leaf dorsal surface.*—Close to 144A to 144B.

6.3.23 *Blotches on leaves of water suckers.*—Little or narrow blotches.

Inflorescence/male bud:

6.4.1 *Peduncle length.*—About 31 cm to 60 cm.

6.4.2 *Empty nodes on peduncle.*—None or occasionally one.

6.4.3 *Peduncle width.*—About 12 cm.

6.4.4 *Peduncle color.*—Close to 144A.

6.4.5 *Peduncle hairiness.*—Hairless.

6.4.6 *Bunch position.*—Hanging at about 45°.

6.4.7 *Bunch shape.*—Cylindrical.

6.4.8 *Bunch appearance.*—Compact; one can easily place one's finger, but not one's hand, between the hands of fruit.

6.4.9 *Flowers that form the fruit.*—Female.

6.4.10 *Fruits.*—Biseriate.

6.4.11 *Rachis type.*—Present; male bud may be degenerated or persistent.

6.4.12 *Rachis position.*—Falling vertically.

6.4.13 *Rachis appearance.*—Bare.

6.4.14 *Male bud type.*—Degenerating before maturity.

6.4.15 *Male bud shape.*—Ovoid.

6.4.16 *Male bud size.*—Length: About 28.0 cm. Diameter, at the widest section: About 22.5 cm.

Bract:

6.5.1 *Bract base shape.*—Large shoulder.

6.5.2 *Bract apex shape.*—Slightly pointed to intermediate.

6.5.3 *Bract imbrication.*—Young bracts slightly overlap.

6.5.4 *Color of the bract external face.*—Close to 187A.

6.5.5 *Color of the bract internal face.*—Close to 178A to 178C basally.

6.5.6 *Color on the bract apex.*—Not tinted with yellow, color is uniform until apex.

6.5.7 *Color stripes on bract.*—With discolored lines on external face.

6.5.8 *Bract scars on rachis.*—Very prominent.

6.5.9 *Fading of color on bract base.*—Color discontinuing towards the base.

6.5.10 *Male bract shape.*—Ovate.

6.5.11 *Male bract lifting.*—Lifting one at the time.

6.5.12 *Bract behavior before falling.*—Not revolute, not rolling.

6.5 13 *Wax on the bract.*—Moderately waxy.

6.5.14 *Presence of grooves on the bract.*—Moderate grooving; parallel ridges are distinguishable.

Male flower:

6.6.1 *Male flower behavior.*—Falling after the bract.

6.6.2 *Compound tepal basic color.*—Close to between NN155A and 11D.

6.6.3 *Compound tepal pigmentation.*—Very few or no visible sign of pigmentation.

6.6.4 *Lobe color of compound tepal.*—Close to between 9D and 10D.

6.6.5 *Lobe development of compound tepal.*—Developed.

6.6.6 *Free tepal color.*—Translucent white.

6.6.7 *Free tepal shape.*—Oval.

6.6.8 *Free tepal appearance.*—More or less smooth.

6.6.9 *Free tepal apex development.*—Very developed.

6.6.10 *Free tepal apex shape.*—Thread-like.

6.6.11 *Anther exertion.*—Same level.

6.6.12 *Filament color*.—Close to NN155A.
6.6.13 *Anther color*.—Close to NN155A.
6.6.14 *Pollen sac color*.—Close to NN155A.
6.6.16 *Style basic color*.—Close to NN155A.
6.6.17 *Pigmentation on style*.—Purple.
6.6.18 *Style exertion*.—Same level.
6.6.19 *Style shape*.—Straight.
6.6.20 *Stigma color*.—Close to 94D.
6.6.21 *Ovary shape*.—Arched.
6.6.22 *Ovary basic color*.—Close to 11D.
6.6.23 *Ovary pigmentation*.—Very few or no visible sign of pigmentation.
6.6.24 *Dominant color of male flower*.—Cream.
6.6.26 *Arrangement of ovules*.—Two-rowed.

Fruit:

6.7.1 *Fruit position*.—Perpendicular to the stalk.
6.7.2 *Number of fruits*.—About 13 to 16 per hand.
6.7.3 *Fruit length*.—About 20.5 cm.
6.7.4 *Fruit shape*.—Straight or slightly curved to straight in the distal part.
6.7.5 *Transverse section of fruit*.—Slightly ridged.
6.7.6 *Fruit apex*.—Blunt-tipped to bottle-necked.
6.7.7 *Remains of flower relicts at fruit apex*.—Without any floral relicts.
6.7.8 *Fruit pedicel length*.—About 38 mm.
6.7.9 *Fruit pedicel width*.—About 12 mm.
6.7.10 *Pedicel surface*.—Hairless.
6.7.11 *Fusion of pedicels*.—Very partially or no visible sign of fusion.
6.7.12 *Immature pedicel and fruit peel color*.—Close to 143B to 143C.
6.7.13 *Mature pedicel and fruit peel color*.—Close to between 14C and 13C.
6.7.14 *Fruit peel thickness*.—About 3 mm.
6.7.15 *Adherence of the fruit peel*.—Fruit peels easily.
6.7.16 *Crack in fruit peel*.—Without cracks.
6.7.17 *Pulp in fruit*.—With pulp.
6.7.18 *Pulp color before maturity*.—Close to NN155D.
6.7.19 *Pulp color at maturity*.—Cream NN155A.
6.7.20 *Fruit fall from hands*.—Persistent.
6.7.21 *Flesh texture*.—Firm.
6.7.22 *Predominant taste*.—Sweet and acid.
6.7.23 *Presence of seeds with source of pollen*.—None.
6.7.24 *Seed surface*.—Not applicable.
6.7.25 *Seed shape*.—Not applicable.

Additional descriptors:

*Days from planting until bunching*.—About 395 days.
*Days from planting until harvest*.—About 573 days.
*Number of leaves at harvest*.—About eight to ten.
*Bunch weight*.—About 30.2 kg.
*Number of hands per bunch*.—About 10 to 13.
*Finger diameter*.—About 14.0 cm.
*Fruit discoloration*.—Fruits of plants of the new *Musa* resist discoloration (browning) when cut for more than twelve hours.

Pathogen resistance & tolerance: Plants of the new *Musa* have been observed to have complete resistance to Panama Disease Tropical Race 1 (*Fusarium oxysporum cubense* Race 1); strong resistance to Panama Disease Tropical Race 4 (*Fusarium oxysporum cubense* Race 4); and strong tolerance to Yellow Sigatoka Leaf Spot (*Pseudocercospora musicola*).

Pest susceptibility & tolerance: In Australian plantation evaluations, no pesticides have been applied to plants of the new *Musa*; and to date, no pest problems have been observed on plants of the new *Musa*. Additionally, fruits of plants of the new *Musa* have been observed to have low susceptibility to marking as a result of birds perching; the low susceptibility is due to the drooping bunch position of the fruits.

Temperature tolerance: Plants of the new *Musa* have been observed to have relatively strong cold temperature tolerance in sub-tropical environments.

It is claimed:

1. A new and distinct *Musa* plant named 'FLF-1' as illustrated and described.

* * * * *